United States Patent [19]

Psaros

[11] Patent Number: 5,727,545
[45] Date of Patent: Mar. 17, 1998

[54] GAS MIXING SYSTEM FOR AN ANAESTHETIC APPARATUS

[75] Inventor: Georgios Psaros, Tullinge, Sweden

[73] Assignee: Siemens Elema AB, Solna, Sweden

[21] Appl. No.: 643,890

[22] Filed: May 7, 1996

[30] Foreign Application Priority Data

Jun. 2, 1995 [SE] Sweden ................................. 9502033

[51] Int. Cl.$^6$ .................................................. A61M 16/00
[52] U.S. Cl. ................................. 128/203.12; 128/203.14; 128/203.24; 128/203.25; 128/204.22
[58] Field of Search ........................... 128/203.12, 203.24, 128/203.14, 203.16, 204.14, 205.11, 200.21, 203.25, 204.22

[56] References Cited

U.S. PATENT DOCUMENTS

| 4,313,436 | 2/1982 | Schwanbom et al. | 128/203.12 |
| 4,770,168 | 9/1988 | Rusz et al. | 128/203.12 |
| 5,256,594 | 10/1993 | Olsson et al. | 128/204.18 |

FOREIGN PATENT DOCUMENTS

| 0 496 336 | 7/1992 | European Pat. Off. | A61M 16/18 |
| 4105971 | 8/1992 | Germany | 128/203.25 |
| 2150034 | 6/1985 | United Kingdom | 128/203.12 |
| 2176313 | 12/1986 | United Kingdom | 128/203.12 |
| WO 92/19302 | 11/1992 | WIPO | A61M 16/18 |

*Primary Examiner*—Vincent Millin
*Assistant Examiner*—V. Srivastava
*Attorney, Agent, or Firm*—Hill, Steadman & Simpson

[57] ABSTRACT

A gas-mixing system for anaesthetic apparatuses has a vaporizer unit for liquid anaesthetic, a first gas line carrying a specific first flow of gas to the vaporizer unit, and a second gas line carrying a second flow of gas past the vaporizer unit. The first gas flow and the second gas flow jointly constitute a total flow of respiratory gas. A first flow regulator is arranged to regulate total flow, and a second flow regulator is arranged to regulate the second flow according to the difference between total flow and a reference value for the first flow.

6 Claims, 1 Drawing Sheet

GAS MIXING SYSTEM FOR AN ANAESTHETIC APPARATUS

BACKGROUND OF THE INVENTION

1. Field of the Invention

The present invention relates to a gas-mixing system for an anaesthetic apparatus for supplying a respiratory gas and an anaesthetic to the breathing system of a subject.

2. Description of the Prior Art

Anesthesia is primarily administered in conjunction with surgery in order to render the patient, a person or a domesticated animal, unconscious. In addition to inducing narcosis, the anaesthetic apparatus must also be able to maintain the patient's respiration, whenever necessary. The respiratory gas supplied to the patient usually contains oxygen, nitrous oxide and, sometimes, air in predefined proportions. Anaesthetic gas, supplied in a gas-mixing system in the anaesthetic apparatus, is also added. At most, the anaesthetic gas amounts to one or a few percent by volume of the total respiratory gas, depending on the anaesthetic gas used. Higher concentrations of the anaesthetic, however, are supplied to the patient during the initial phase of anesthesia induction in order to achieve patient narcosis more rapidly and to achieve a saturation concentration of anaesthetic in the patient's body. "Respiratory gas" as used herein means a gas mixture without any anaesthetic gas. The designation "final respiratory gas" will henceforth be used for the gas sent to the breathing circuit and the patient, i.e. respiratory gas plus anaesthetic gas.

In the anaesthetic apparatus, bulk anaesthetic is usually present in liquid form and is vaporized into a gas in a vaporizer unit in the gas-mixing system. A predefined amount of anaesthetic gas can be supplied to the patient when one or more of the other gases is passed through the vaporizer. A large number of different kinds of vaporizers are well-known in the anesthesia art. with some vaporizers, therefore, some or all of the respiratory gas passes through the vaporizer unit. With other vaporizers, only one gas component of the respiratory gas passes through the vaporizer.

The amount of anaesthetic which must be added to gas passing through the vaporizer depends on the breathing circuit connected to the patient. In principle, two different breathing system are employed. one is the open circuit system in which only freshly mixed final respiratory gas (with anaesthetic gas) is supplied to the patient. All expired gas from the patient is removed from the apparatus via an evacuation unit in which expensive anaesthetic can be recovered. The second system is the rebreathing system in which a large or small part of the patient's expired gases is returned to the patient in the next consecutive inspiration. The most extreme rebreathing circuit system is the closed system in which virtually all respiratory gas is returned to the patient. In this system, carbon dioxide is removed by a carbon dioxide absorber, and a small amount of fresh respiratory gas is added to the rebreathed respiratory gas to compensate for minor leakage and for gas intake (primarily oxygen and anaesthetic gas) in the patient's body.

The open system thus has a relatively heavy consumption of anaesthetic, and gas flow through the vaporizer is relatively large. In the closed system, anaesthetic consumption is minimal, and gas flow through the vaporizer is therefore relatively small. It should be noted, however, that the relatively large flow through the vaporizer for the open system is small in relation to the total flow of gas through the anaesthetic apparatus.

A gas-mixing system for anaesthetic apparatuses is described in European Application 0 496 336. This known apparatus is able to operate according to both breathing systems, and the gas-mixing system is devised in the following manner. Component gases which will form the respiratory gas are connected to the apparatus by different gas connectors, a flow regulator being arranged for each gas connector. Gas fed to the vaporizer unit is controlled in one of the connectors. The other gas connectors are connected to a mixing chamber in which the gases are mixed. Downstream from the vaporizer unit, the two gas flows join, and the final respiratory gas is mixed before being delivered to the patient. The flow regulator is controlled so that the final respiratory gas contains the various component gases in predefined concentrations.

As already noted, gas flow through the vaporizer depends on the breathing system. In one embodiment, only anaesthetic gas is rebreathed. This means that only an extremely small amount of gas need pass through the vaporizer unit. Achieving exact control of extremely small flows has proved to be difficult. Exact regulation of the gas passing in every situation, however, is important in vaporizer units in which gas flowing through them is to be saturated with anaesthetic gas, thereby picking up a specific amount of anaesthetic gas. The flow regulator must also be capable of regulating flows of varying magnitude without the need for complex adjustments to the equipment. One such flow regulator is known from U.S. Pat. No. 5,265,594. This known flow regulator consists of a solenoid valve with a membrane arranged at a valve seat. This known flow regulator must operate virtually in a closed position when regulating extremely small flows. Problems could then arise because of adhesion between the flow regulator's membrane and the valve seat.

Another known gas-mixing system for anaesthetic apparatuses is described in European Application 0 585 251. This apparatus separates gas which is to pass through a vaporizer unit and gas which is not to pass through the vaporizer unit in some other way. A total gas flow enters via a line subdivided into two branches. The first branch leads to the vaporizer unit, and the second branch leads to a mixing chamber. The second branch contains a back pressure valve which opens at a given pressure and allows gas to pass. This valve is used to control a specific, maximum gas flow into the first branch. If the total gas flow is so small that it fails to generate the valve opening pressure, flow can amount to any value. Counter-pressure in the valve is generated by a spring, therefore controlling flow through the first branch is difficult. This apparatus is equipped with an anaesthetic pump, which pumps specific amounts of anaesthetic fluid into the passing gas flow, in order to add specific amounts of anaesthetic.

In principle, therefore, the gas-mixing system according to European Application 0 585 251 is limited to vaporizer units containing a pump for feeding anaesthetic fluid into the passing flow of gas. Since gas flow through the vaporizer unit is generally constant (about 1 liter a minute is stated in the description), the system is not suitable when there are large variations in the supply of anaesthetic to the breathing circuit. In closed systems, for example, a flow of 1 liter a minute is much too high, since the corresponding amount of respiratory gas must then be discharged from the breathing circuit.

SUMMARY OF THE INVENTION

An object of the invention is to provide a gas-mixing system for anaesthetic apparatuses, which can be used for all types of breathing systems and with all known types of vaporizer units, which solves the above-described problems.

The above object is achieved in accordance with the principles of the present invention in a gas-mixing system for an anaesthetic apparatus having a vaporizer unit for liquid anaesthetic, wherein a first line carrying a specific first flow of gas to the vaporizer unit is provided, as well as a second line carrying a second flow of gas past the vaporizer unit. The first gas flow and the second gas flow jointly constitute a total flow of respiratory gas. A first flow regulator is arranged to regulate total flow, and a second flow regulator is arranged to regulate the second flow according to the difference between the total flow and a reference value for the first flow.

Instead of trying to regulate a minimum flow of gas to the vaporizer unit with extreme accuracy with one flow regulator, the inventive system utilizes flow regulators to regulate large flows with extreme accuracy, i.e., the total flow of respiratory gas and the flow of respiratory gas which is not to pass the vaporizer unit. These gas flows are then regulated such that the difference in their respective flows forms the desired flow through the vaporizer unit. It is possible to achieve this with known, electronically controlled flow regulators, such as the aforementioned known flow regulator.

DESCRIPTION OF THE PREFERRED EMBODIMENTS

Figure 1:
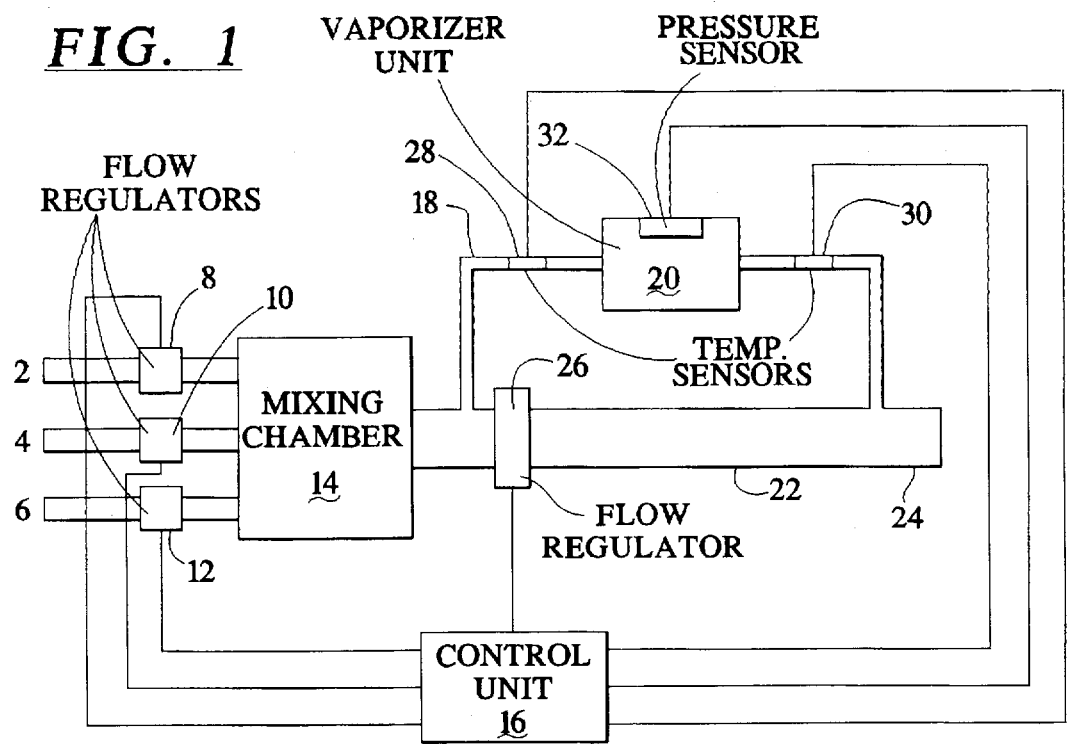
FIG. 1 shows a first embodiment of a gas-mixing system according to the invention.

FIG. 1 shows, in a first embodiment of the inventive gas-mixing system, the gas-mixing system's basic components. Three gas connectors 2, 4 and 6 for the component gases in the respiratory gas are connected to the gas-mixing system. Nitrous oxide is preferably connected to the gas connector 2, oxygen to the second gas connector 4 and air, or additional oxygen, to the third connector 6. The third gas connector 6 can alternatively be kept closed. Respective flow regulators 8, 10 and 12 are arranged in the gas connectors 2, 4 and 6 to regulate the respective gas flow, so a predefined total flow of respiratory gas components is sent to a mixing chamber 14 for mixing.

The flow regulators 8, 10 and 12 are controlled by a control unit 16. Control is based on gas pressures and gas flows measured in the known manner, e.g., as described for the known flow regulator in U.S. Pat. No. 5,265,594 (thus pressure and/or flow sensors are not shown in the figure).

After the mixing chamber, the total flow of respiratory gas is split into two branches. A first flow of respiratory gas is passed through a first gas line 18 to a vaporizer unit 20 in which a specific amount of anaesthetic gas is added to the first flow of respiratory gas. In principle, any kind of known vaporizer unit 20 can be used, especially the kind in which gas passing through the vaporizer unit 20 becomes saturated with anaesthetic gas.

A second flow of respiratory gas is passed through a second gas line 22 to a connecting line 24 to which the first gas line 18 connects and in which the final respiratory gas is mixed before being carried to a breathing circuit and the patient (not shown in the figure) connected thereto. The breathing circuit can be devised for all known types of breathing systems, from open systems to completely closed systems.

A second flow regulator 26 is arranged in the second gas line 22 to regulate the flow of respiratory gas through the second gas line 22. The second flow regulator 26 is controlled by the control unit 16 and can be constructed according to the aforementioned known flow regulator of U.S. Pat. No. 5,265,594. Control can, e.g., be exercised so the control unit 16 receives information on the total flow of respiratory gas (via flowmeters or from control of total respiratory gas flow) and a reference value for the flow of respiratory gas which is to be passed through the first gas line 18 (programmed or calculated from the current need for anaesthetic gas). The control unit 16 then calculates the difference between these two values and employs the difference as a reference value in controlling the second flow regulator 26. Exact regulation of a relatively large flow is easier to control with the known regulator, since it can then operate in an open position, and no problems with membrane adhesion to the valve seat ever arise. Since both total flow and flow in the second gas line 22 are controlled with extreme accuracy, the flow of surplus respiratory gas carried to the vaporizer unit 20 in the first gas line 18, will also have the same extreme accuracy.

Refined control is achieved when a first temperature sensor is arranged before the vaporizer unit 20, a second temperature sensor 30 is arranged after the vaporizer 20 and a pressure sensor 32 is arranged inside the vaporizer 20. The temperature gradient before and after the vaporizer unit 20 designates thermodynamic impact in vaporization, and pressure measurement supplies information on conditions in the vaporizer unit 20. These parameters can be sent to the control unit 16 which, in regulating the second flow regulator 26, can take their impact into account on gas flows.

Figure 2:
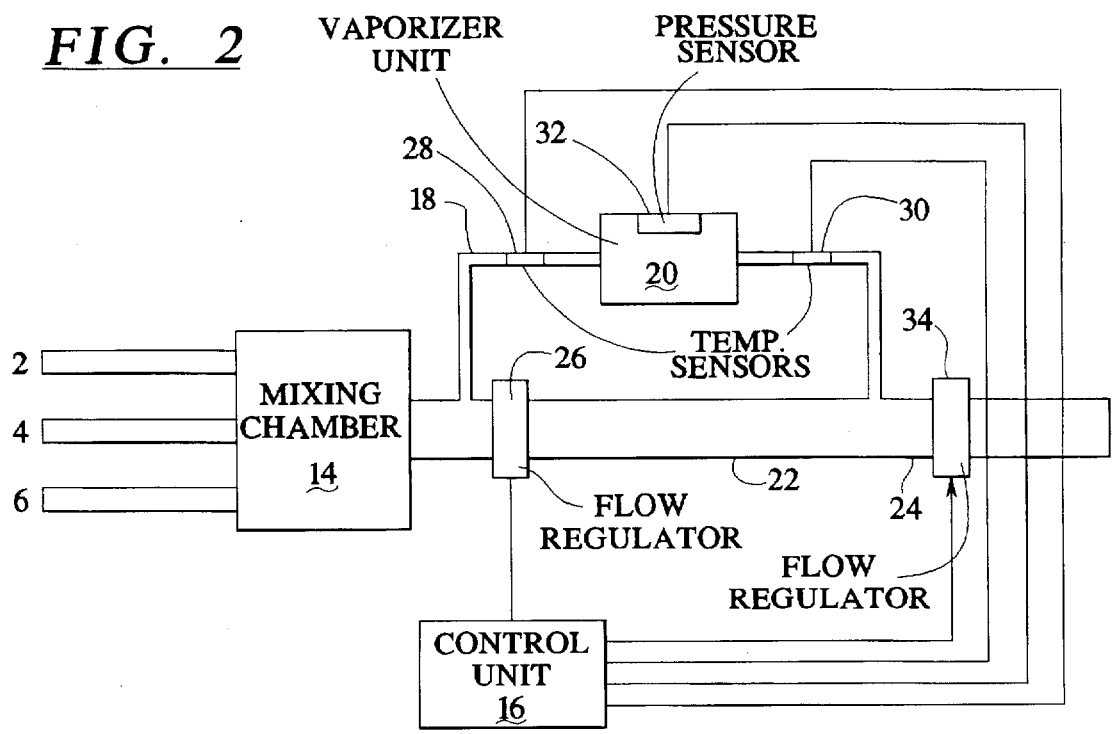
FIG. 2 shows a second embodiment of the inventive gas-mixing system.

A second embodiment of the inventive gas-mixing system is shown in FIG. 2. Since it agrees in many respects with the first embodiment in FIG. 1, identical elements and elements with the same function have been assigned the same designations. The main difference is that a first flow regulator 34 for regulating total respiratory gas flow is arranged downstream from the vaporizer unit 20. The addition of gas components via the gas connectors 2, 4 and 6 is then appropriately performed in fixed proportions. If, for example, pressure is the same in all gas connectors 2, 4 and 6, the proportions can be controlled with fixed valve openings, back pressure valves or the like, however, the principle for attaining flow through the first gas line 18 is basically the same. The first flow regulator 34 passes a predefined final flow of respiratory gas, i.e. including anaesthetic gas. The second flow regulator 26 is then regulated so it passes the difference between the final flow of respiratory gas and the sum of the flow of anaesthetic gas plus the target flow in the first gas line 18. The total flow of respiratory gas is obtained when compensation is made for the contribution of the anaesthetic gas to the final flow of respiratory gas. The flow of anaesthetic gas is known, since a specific amount of anaesthetic gas is added to the respiratory gas which is passed through the vaporizer unit 20.

Although modifications and changes may be suggested by those skilled in the art, it is the intention of the inventors to embody within the patent warranted hereon all changes and modifications as reasonably and properly come within the scope of their contribution to the art.

I claim as my invention:

1. A gas-mixing system for an anaesthetic apparatus for supplying a respiratory gas and an anaesthetic to a breathing system of a living subject comprising:

a vaporizer unit containing a liquid anaesthetic;

a source of respiratory gas;

a first gas line connected between said source of respiratory gas and said vaporizer unit for carrying a first flow of respiratory gas from the source of respiratory gas through the vaporizer unit, said vaporizer unit adding a specific amount of anaesthetic to said first flow of respiratory gas;

a connecting body disposed downstream of said vaporizer unit;

a second gas line connected between said source of respiratory gas and said connecting body for carrying a second flow of respiratory gas from said source of respiratory gas past said vaporizer unit, said first and second flows being combined in said connecting body to form a total flow of respiratory gas, with a sum of said first flow plus said second flow forming said total flow;

a first flow regulator means for regulating said total flow of respiratory gas;

a second flow regulator means connected for interacting with said second gas line to regulate said second flow of respiratory gas;

means for obtaining a reference value for said first flow of respiratory gas; and control means for controlling said second flow regulator means for causing said second flow or respiratory gas to be substantially equal to a difference between said total flow of respiratory gas and said reference value.

2. A gas-mixing system as claimed in claim 1 wherein said vaporizer unit comprises means for saturating respiratory gas flowing through the vaporizer unit with anaesthetic before said second flow of respiratory gas reaches said connecting body.

3. A gas-mixing system as claimed in claim 1 wherein said source of respiratory gas comprises a first source of a first respiratory gas and a second source of a second respiratory gas, different from said first respiratory gas, and mixing means for, connected between said first and second sources and a beginning of said first gas line, for mixing said first and second respiratory gases to form said first flow of respiratory gas.

4. A gas-mixing system as claimed in claim 3 wherein said first flow regulator means comprises a first flow regulator connected between said first source and said mixing chamber and a second flow regulator means connected between said second source and said mixing chamber, each of said first and second flow regulators being controlled by said control means.

5. A gas-mixing system as claimed in claim 1 wherein said first flow regulator means is disposed downstream of said connecting body.

6. A gas-mixing system as claimed in claim 1 wherein said means for generating said reference value comprise a first temperature sensor disposed upstream of said vaporizer unit, a second temperature sensor disposed downstream of said vaporizer unit, a pressure sensor disposed in said vaporizer unit, said first and second temperature sensors and said pressure sensor respectively generating output signals, and means in said control unit for generating said reference value from a combination of the outputs of said first and second temperature sensors and said pressure sensor.

* * * * *